US008480690B2

(12) United States Patent
Vijayanagar (10) Patent No.: US 8,480,690 B2
(45) Date of Patent: *Jul. 9, 2013

(54) SUTURE ORGANIZER (76) Inventor: Raghavendra Rao Vijayanagar, Tampa, FL (US)

(*) Notice: Subject to any disclaimer, the term of this patent is extended or adjusted under 35 U.S.C. 154(b) by 100 days.

This patent is subject to a terminal disclaimer.

(21) Appl. No.: 12/804,275

(22) Filed: Jul. 19, 2010

(65) Prior Publication Data

US 2011/0152894 A1 Jun. 23, 2011

Related U.S. Application Data (63) Continuation-in-part of application No. 12/802,302, filed on Jun. 3, 2010, now abandoned, which is a continuation-in-part of application No. 12/653,697, filed on Dec. 17, 2009.

(51) Int. Cl.
*A61B 17/04* (2006.01)

(52) U.S. Cl.
CPC .................................. *A61B 17/04* (2013.01)
USPC ........................ 606/148; 24/598.2; 24/599.8

(58) Field of Classification Search
USPC ....... 606/139, 148; 24/598.2–601.4; 604/177, 604/178, 179, 180
See application file for complete search history.

(56) References Cited

U.S. PATENT DOCUMENTS

| 4,392,853 | A | * | 7/1983 | Muto | 604/171 |
|---|---|---|---|---|---|
| 5,934,408 | A | * | 8/1999 | Flux | 182/5 |
| 6,308,383 | B1 | * | 10/2001 | Schrader | 24/265 H |
| 6,336,260 | B1 | * | 1/2002 | Mauthner | 24/376 |
| D476,218 | S | * | 6/2003 | Kelleghan | D8/356 |
| D484,770 | S | * | 1/2004 | Green | D8/99 |
| 7,125,186 | B1 | * | 10/2006 | Stokes | 401/8 |
| 7,126,484 | B1 | * | 10/2006 | Luquire | 340/574 |
| D572,573 | S | * | 7/2008 | Abels | D8/356 |
| 7,856,699 | B2 | * | 12/2010 | Sorensen et al. | 24/130 |
| 7,922,220 | B2 | * | 4/2011 | Coulombe | 292/1 |
| 8,007,015 | B2 | * | 8/2011 | Coulombe | 292/1 |
| 2002/0179023 | A1 | * | 12/2002 | Axel | 119/801 |
| 2004/0031644 | A1 | * | 2/2004 | Kurtgis | 182/3 |
| 2004/0253038 | A1 | * | 12/2004 | Goldberg | 401/131 |
| 2005/0028331 | A1 | * | 2/2005 | Axel | 24/599.1 |
| 2005/0144730 | A1 | * | 7/2005 | Barber et al. | 7/138 |
| 2006/0162138 | A1 | * | 7/2006 | Kimura | 24/599.6 |
| 2006/0272595 | A1 | * | 12/2006 | Edwards | 119/795 |
| 2008/0120818 | A1 | * | 5/2008 | Belcourt et al. | 24/599.5 |
| 2008/0184540 | A1 | * | 8/2008 | Coulombe | 24/599.1 |
| 2008/0185848 | A1 | * | 8/2008 | Coulombe | 292/1 |
| 2009/0183347 | A1 | * | 7/2009 | Abels | 24/599.6 |
| 2010/0088899 | A1 | * | 4/2010 | Garcia et al. | 30/123 |
| 2010/0306974 | A1 | * | 12/2010 | Munoz | 24/598.8 |
| 2011/0047764 | A1 | * | 3/2011 | Strasser | 24/599.5 |
| 2011/0152893 | A1 | * | 6/2011 | Vijayanagar | 606/148 |

* cited by examiner

*Primary Examiner* — Ryan Severson
*Assistant Examiner* — Jonathan W Miles
(74) *Attorney, Agent, or Firm* — Arthur W. Fisher, III (57) ABSTRACT A suture organizer to maintain a plurality of sutures attached to a patient during a surgical procedure or operation in position relative to each other during the surgical procedure or operation comprising a hemostat retainer including a hemostat retainer member to receive and retain the finger hole or thumb hole of a corresponding hemostat connected to a corresponding suture and a clasp including a pair of clasp members to cooperatively clamp a surgical drape or the like therebetween to hold the suture organizer in position during the surgical procedure or operation.

18 Claims, 9 Drawing Sheets

SUTURE ORGANIZER

CROSS-REFERENCE

This is a continuation-in-part application of Ser. No. 12/802,302 filed Jun. 3, 2010 now abandoned which is a continuation-in-part application of co-pending application of Ser. No. 12/653,697 filed Dec. 17, 2009.

BACKGROUND OF THE INVENTION

1. Field of the Invention

A suture organizer to maintain a plurality of sutures attached to a patient during a surgical procedure or operation in position relative to each other during the surgical procedure of operation.

2. Description of the Prior Art

Many types of surgery require the use of multiple sutures to pull severed muscles, nerves and tendons away from the surgery site. For example, during heart surgery multiple sutures are used to repair the mitral and aortic valves. If the sutures are not properly organized, the sutures can become entangled and complicate the surgeon's job. To aid the surgeon, many suture organizers have been developed, the most common of which is known as the Gabbay-Frater organizer. These heart surgery suture organizers are specific to heart surgery where the patient is supine and motionless.

In particular, during surgery, a surgeon needs ready and efficient access to sutures. Often the suture handling practice has been considered inefficient, clumsy and wasteful. Often sutures were laid out on towels and passed individually to the surgeon when needed. The sutures became entangled and difficult to separate; the suture supply was sometimes spilled or upset.

In addition to the Gabbey-Frater organizer, devices that lay out and retain sutures in a neat and organized fashion before the sutures are needed have been developed. These devices enable the surgical scrub nurse to deftly grasp an individual suture and pass it to the surgeon. However, the surgeon typically attaches numerous sutures to the patient before tying or knotting and cutting the individual sutures. The sutures are typically extended away from the surgical field and laid out on the surgical drape, the sutures being somewhat immobilized by a surgical clamp which is secured to the free end of each suture. Some operations such as vascular surgery require numerous fine sutures which can easily soon crowd the surgical field and become entangled before the surgeon can tie them. Untangling the sutures delays completion of the surgery and increases the trauma of the patient.

U.S. Pat. No. 2,692,599 teaches a ligature holder for surgical operations comprising an elongated relatively stiff base strip, an elongated helical spring, anchor elements carried by the base strip at locations on one side thereof spaced apart along the length of the base strip. Opposite ends of the spring are connected to the respective anchor elements and adjustable means associated with the spring for varying the tension thereof and thereby varying the gripping pressure of adjacent coils of the spring on surgical ligatures between the coils.

U.S. Pat. No. 3,515,129 shows a surgical appliance comprising of an elongated channel shaped strip of flexible plastic having overlapping ends provided with registering apertures to receive a connector for positioning the strip into a generally circular form for emplacement as a retractor in an incision. The strip includes coplanar lateral wings on its side edges and lateral fingers disposed between the wings to define suture holding slits with outer rounded ends of the wings serving as guides for the introduction of sutures from the incised area into the slits. The winged sections are severable from the strip and attachable by connectors to wings on the strip to provide mounting feet in the external incision encompassing placement of the suture holding appliance.

U.S. Pat. No. 4,185,636 disclosures a plurality of organizers each formed with an arcuate support member upon which a plurality of suture holding devices are positioned in spaced relationship one to the other. The organizers are disposed proximate an area of a body upon which surgery is to be performed to facilitate speedy and orderly control of interrupted sutures and needles utilized during the surgical procedure. Each holding device includes a pair of spaced wall members and a resilient holding member disposed in compression therebetween in such a manner that sutures can be releasably held between the resilient member and the adjacent wall member surface.

U.S. Pat. No. 4,274,398 relates to a surgical retractor comprising a frame to fit the surface contour of the portion of the body to be operated on and at least one stay including an elastic member and tissue holding means. The frame has a plurality of notches spaced about its periphery and the elastic member of the stay is adapted to be inserted into one of the notches and held in place by friction to retract the tissue.

U.S. Pat. No. 4,492,229 describes a suture guide holder for releasably securing a "Gabbay-Frater" type suture guide in place adjacent a surgical incision held open by a retractor. The holder includes a rigid frame with a central opening for access to the incision area. The frame is adapted to rest directly on the arms of the retractor. It may also be secured to the surgical drapes at the incision site by spring clips extending downwardly from a bottom side of the frame. Upwardly protruding studs receive towel clip holes of the suture guides, securing the guides in position on the frame adjacent the incision.

U.S. Pat. No. 5,207,703 shows a suture organizer comprises a flat, plate-like member having fingerlike projections extending from an upper surface thereof. A layer of adhesive is provided on a lower surface of the plate-like member in order to adhere to a surgical drape or sheet near the vicinity of a surgical incision. Sutures are received in valleys defined by the projections thereby minimizing entanglement of the sutures after surgical attachment but prior to tying and cutting.

U.S. Pat. No. 7,303,568 teaches a suture clamp and/or suture retainer and organizer device for use during a surgical procedure including an elongated body formed of resilient material having a plurality of spaced lateral slits through one surface. The slits are individually identified and sized to receive and grip a surgical suture. A tapered pocket is located adjacent to and opens into each slit for receiving and retaining the nose of a hemostat attached to a suture. The device may be attached by adhesive backing or by clamps to a surgical drape or other support surface.

U.S 2003/0055439 relates to an apparatus for holding and arranging threads in surgical operations with a flexible structure including a ring form connecting straight linear forms or divided linear forms. V shape ditches are cut on the upper portion. The threads are accurately held and arranged without any tangling with other threads.

Thus there is a need for a device that will neatly and efficiently organize and retain sutures during surgery.

SUMMARY OF THE INVENTION

The present invention relates to a suture organizer for use during a surgical procedure or operation on a patient protected by surgical drape.

The suture organizer comprises a hemostat retainer to retain a plurality of hemostats and a clasp to clamp the suture organizer to the surgical drape.

The hemostat retainer comprises a hemostat retainer member having a plurality of grooves to receive a finger hole or a thumb hole of a hemostat gripping a suture attached to the patient. An enlarged arcuate member is formed on one end portion of the hemostat retainer member, while, a reduced arcuate member is formed on the opposite end portion of the hemostat retainer member. A retainer closure member is pivotally coupled to the reduced arcuate member and biased in a normally closed position to engage and interlock with the enlarged member as described more fully hereinafter.

The clasp comprises a first clasp member having a first grasping element formed thereon and a second clasp member having a second grasping element pivotally coupled to the reduced arcuate member and biased in a normally closed position such that the first grasping element and the second grasping element grasp or clamp the surgical drape therebetween to attach the suture organizer to the surgical drape.

Once the surgeon has attached sutures to the patient, each suture with the corresponding surgical clamp or hemostat secured thereto is extended away from the surgical field. With the retainer closure member held open against the force of the bias or spring, the surgical clamps or hemostats are positioned on the hemostat retainer member with the finger hole or thumb hole placed into a corresponding groove. Once so positioned, the retainer closure member is released allowing the force of the bias or spring to close the retainer closure member.

The suture organizer is attached or secured to the surgical drape by separating the first grasping element and the second clasping element against the force of the bias. When the clasp is open, a portion of the surgical drape is placed in the opening between the first grasping element and the second clasping element. The bias then closes the second clasp member such that the first grasping element and the second clasping element engage each other grasping the surgical drape.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature and object of the invention, reference should be had to the following detailed description taken in connection with the accompanying drawings in which.

Similar reference characters refer to similar parts throughout the several views of the drawings.

DETAILED DESCRIPTION OF THE INVENTION

Figure 1:
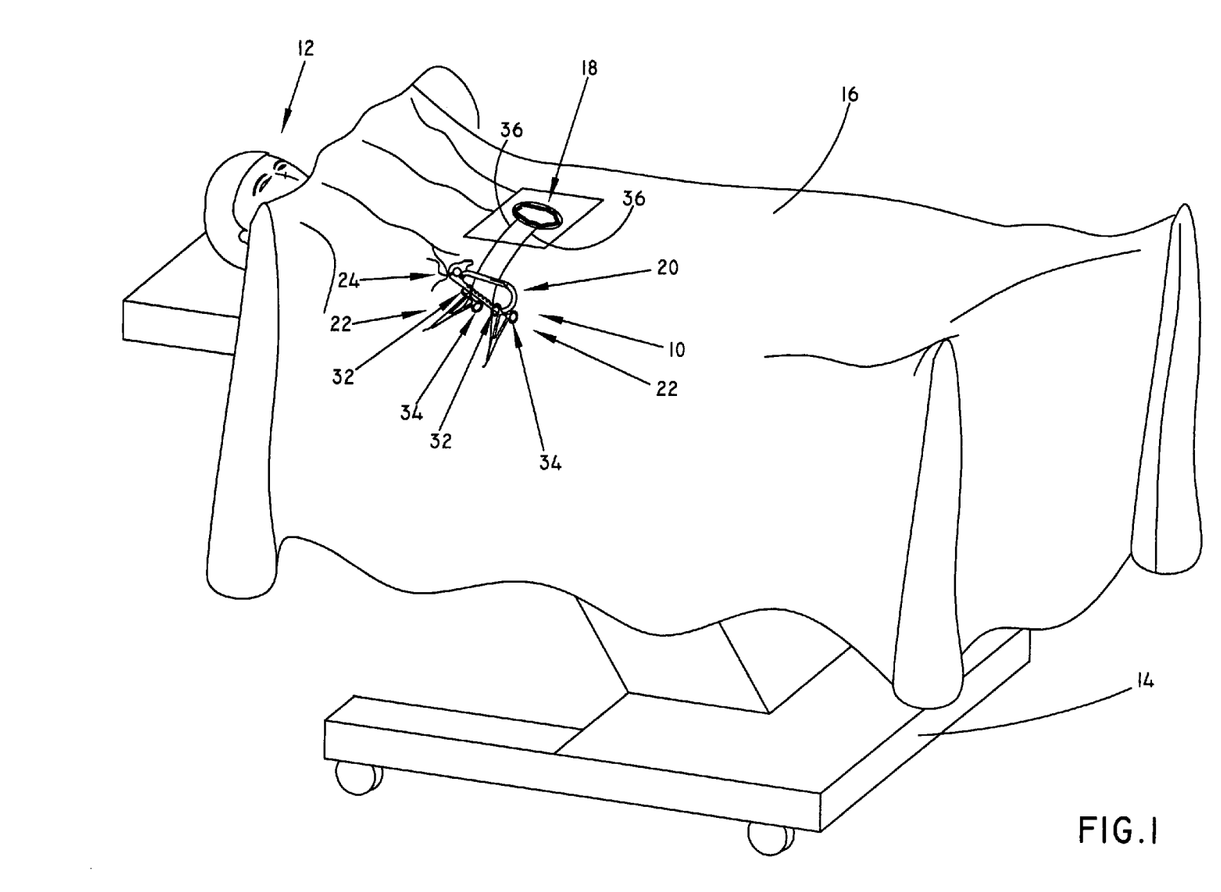
FIG. 1 is a perspective view of a patient on an operating table protected by a surgical drape with the surgical retainer device of the present invention in use.
Figure 2:
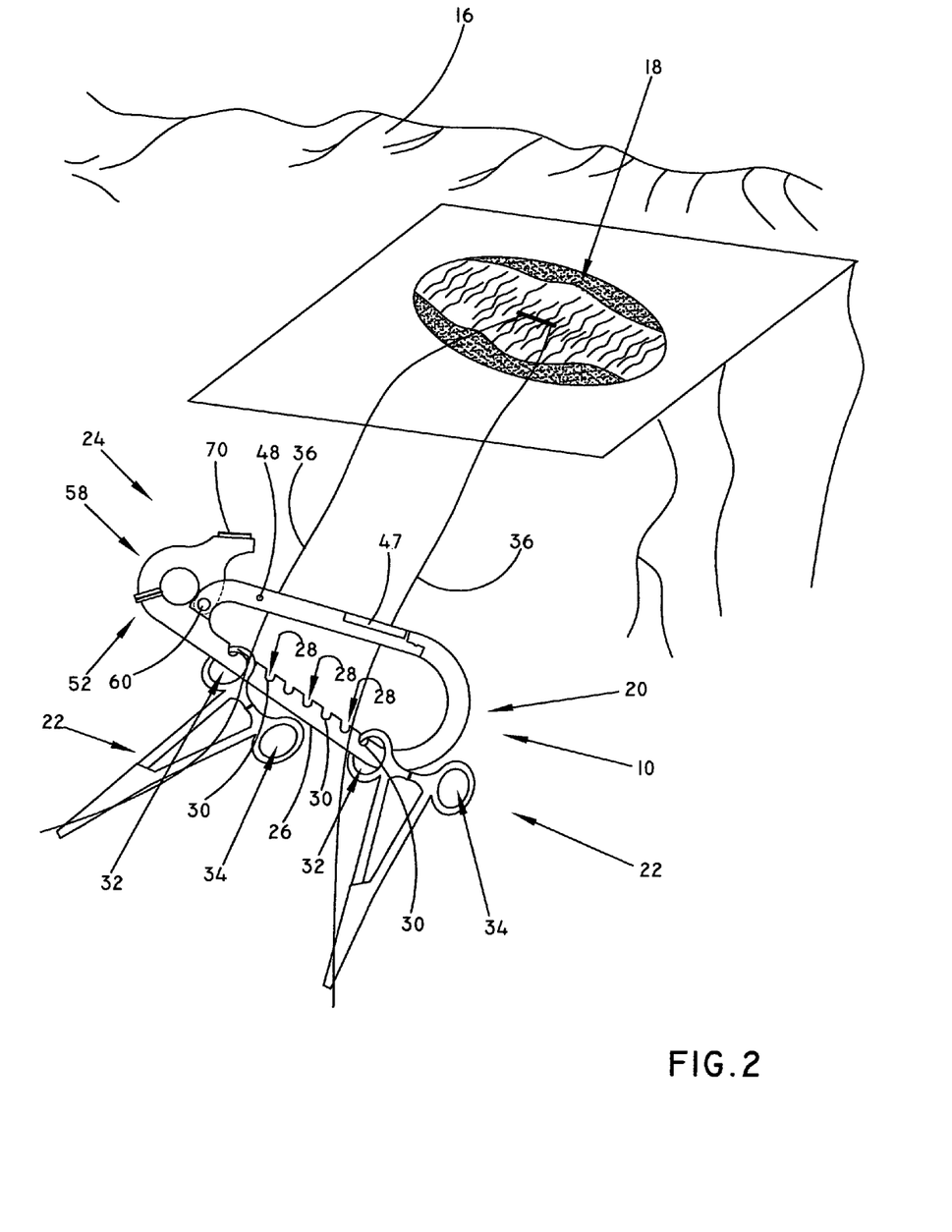
FIG. 2 is an enlarged view of the patient on an operating table protected by a surgical drape with the surgical retainer device of the present invention in use shown in FIG. 1.

As shown in FIGS. 1 and 2, the present invention relates to a suture organizer generally indicated as 10 for use during a surgical procedure or operation on a patient generally indicated as 12 on an operating table 14 protected by a surgical drape 16 with the surgical field generally indicated as 18 exposed.

As shown in FIGS. 1 and 2, the suture organizer 12 comprises a hemostat retainer generally indicated as 20 to retain a plurality of surgical clamps or hemostats each generally indicated as 22 and a clasp generally indicated as 24 to clamp the suture organizer 10 to the surgical drape 16.

Figure 3:
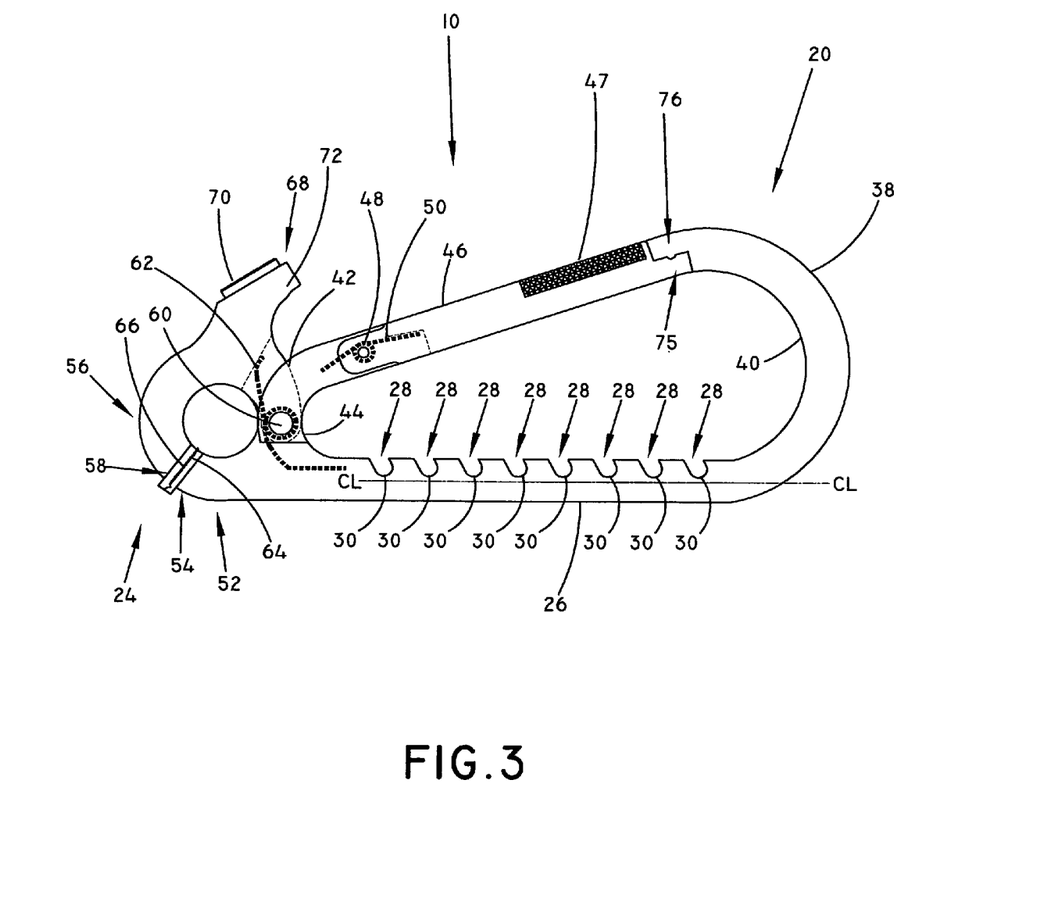
FIG. 3 is a side view of the surgical retainer device of the present invention.
Figure 4:
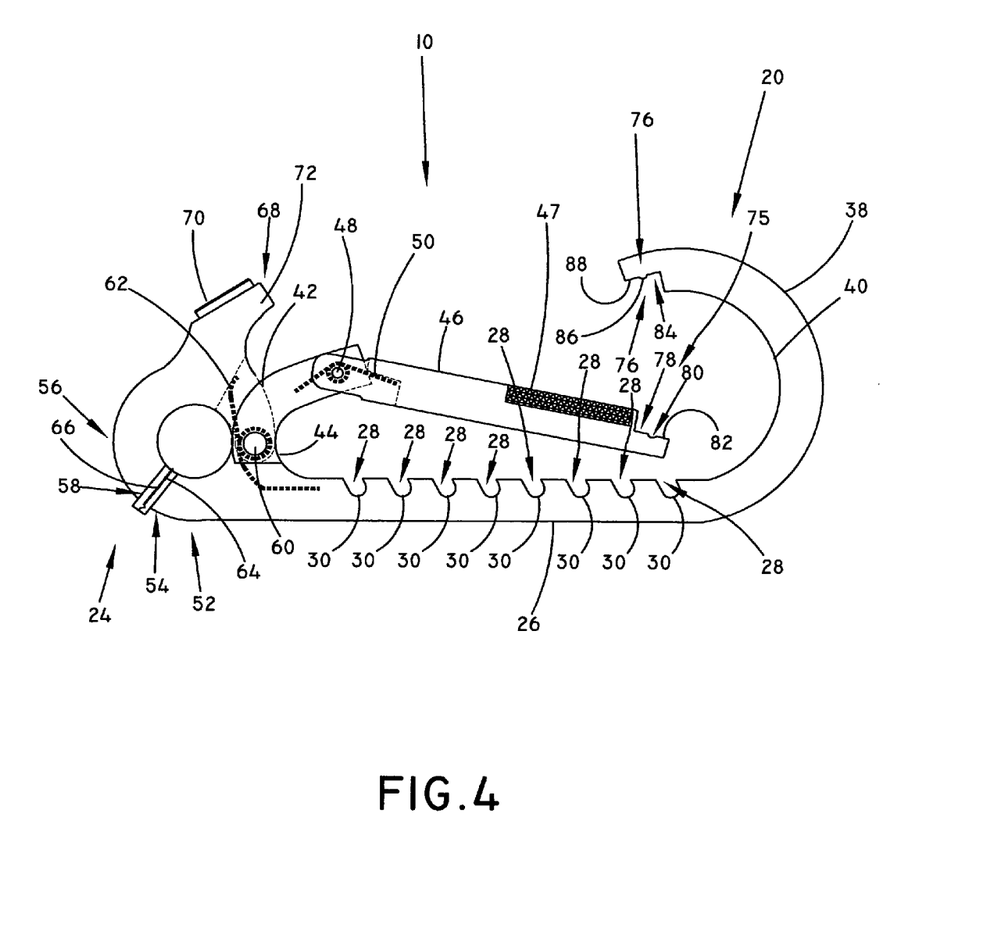
FIG. 4 is a side view of the surgical retainer device of the present invention with the retainer closure arm or retainer in the open position.
Figure 5:
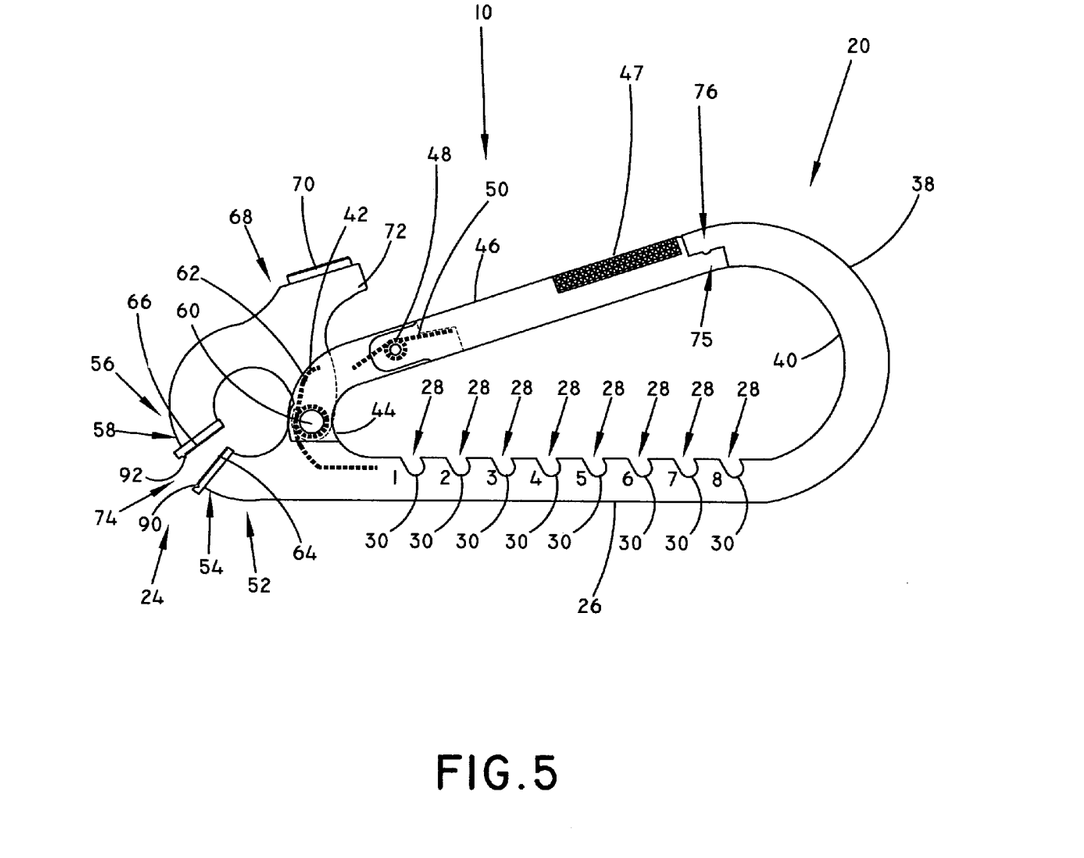
FIG. 5 is a side view of the surgical retainer device of the present invention with the retainer clasp in the open position.

As best shown in FIGS. 3 through 5, the hemostat retainer 20 comprises hemostat retainer member 26 having a plurality of grooves each indicated as 28 each terminating in an inner concave terminus 30 to receive a finger hole 32 or a thumb hole 34 of a surgical clamp or hemostat 22 gripping a suture 36 attached to the patient as described more fully hereinafter. Each groove 28 is inclined on a diagonal line relative to the longitudinal center-line CL of the hemostat retainer member 26. An enlarged arcuate substantially U-shaped member 38 having a substantially concave inner surface 40 is formed on one end portion of the hemostat retainer member 26; while, a reduced arcuate substantially C-shaped member 42 having a substantially concave inner surface 44 is formed on the opposite end portion of the hemostat retainer member 26. A retainer closure member 46 including knurled or rough surface 47 formed on the outer or free end portion thereof is pivotally coupled to the reduced arcuate substantially C-shaped member 42 by a pivot pin 48 and biased in a normally closed position (FIGS. 3 and 5) by a bias or spring 50 to engage and interlock with the enlarged substantially U-shaped member 38 as described more fully hereinafter.

As best shown in FIGS. 3 through 5, the clasp 24 comprises a first clasp member generally indicated as 52 formed on the hemostat retainer member 26 adjacent the reduced arcuate substantially C-shaped member 42 having a first grasping element generally indicated as 54 formed thereon and a second clasp member generally indicated as 56 having a second grasping element generally indicated as 58 pivotally coupled to the reduced arcuate substantially C-shaped member 42 by a pivot pin 60 and biased in a normally closed position (FIGS. 3 and 4) by a bias or spring 62 such that the first grasping element 54 and the second grasping element 58 grasp or clamp the surgical drape 16 therebetween to attach the suture organizer 10 to the surgical drape 16. The first grasping element 54 and the second grasping element 58 include a knurled or rough surface indicated as 64 and 66 respectively to increase or enhance the grasping or clamping effect therebetween on the surgical drape 16. An actuator or opening member generally indicated as 68 including a knurled or rough surface 70 is formed on an extension 72 formed on the second clasp member 56 to facilitate movement or opening of the second clasp member 52 to separate the first grasping element 54 and the second grasping element 58 relative to each other to create a space 74 therebetween to receive the surgical drape 16 therebetween (FIG. 5).

As best shown in FIG. 4, the hemostat retainer 20 may further comprise an interlocking mechanism including a first interlocking element generally indicated as 75 formed on the outer end portion of the enlarged arcuate substantially U-shaped member 38 and a second interlocking element generally indicated as 76 formed on the outer end portion of the retainer closure member 46.

The first interlocking element 75 and the second interlocking element 76 include a first indentation 78 having a recess 80 formed in the mid-portion of the inner surface 82 thereof and a second indentation 84 having a protrusion 86 formed on the mid portion of the inner surface 88 thereof respectively such that the inner surfaces 82 and 88 engage each other and the protrusion 86 is disposed within the recess 80 to align the retainer closure member 46 with the outer end portion of the enlarged substantially U-shaped member 38 when the retainer closure member 46 is in the closed position under the force of the bias or spring 50 (FIGS. 3 and 5).

As best shown in FIG. 5, the clasp 24 may further comprise an interlocking mechanism including a first interlocking element or recess 90 formed in the first grasping element 54 and a second interlocking or alignment element or protrusion 92 formed on the second grasping element 58 such that the first grasping element 54 and the second grasping element 58 engage each other and the protrusion 92 is disposed within the recess 90 to align the first grasping element 54 and the second grasping element 58 relative to each other when the second clasp member 56 is in the closed position under the force of the bias or spring 62 (FIGS. 3 and 4).

Figure 6:
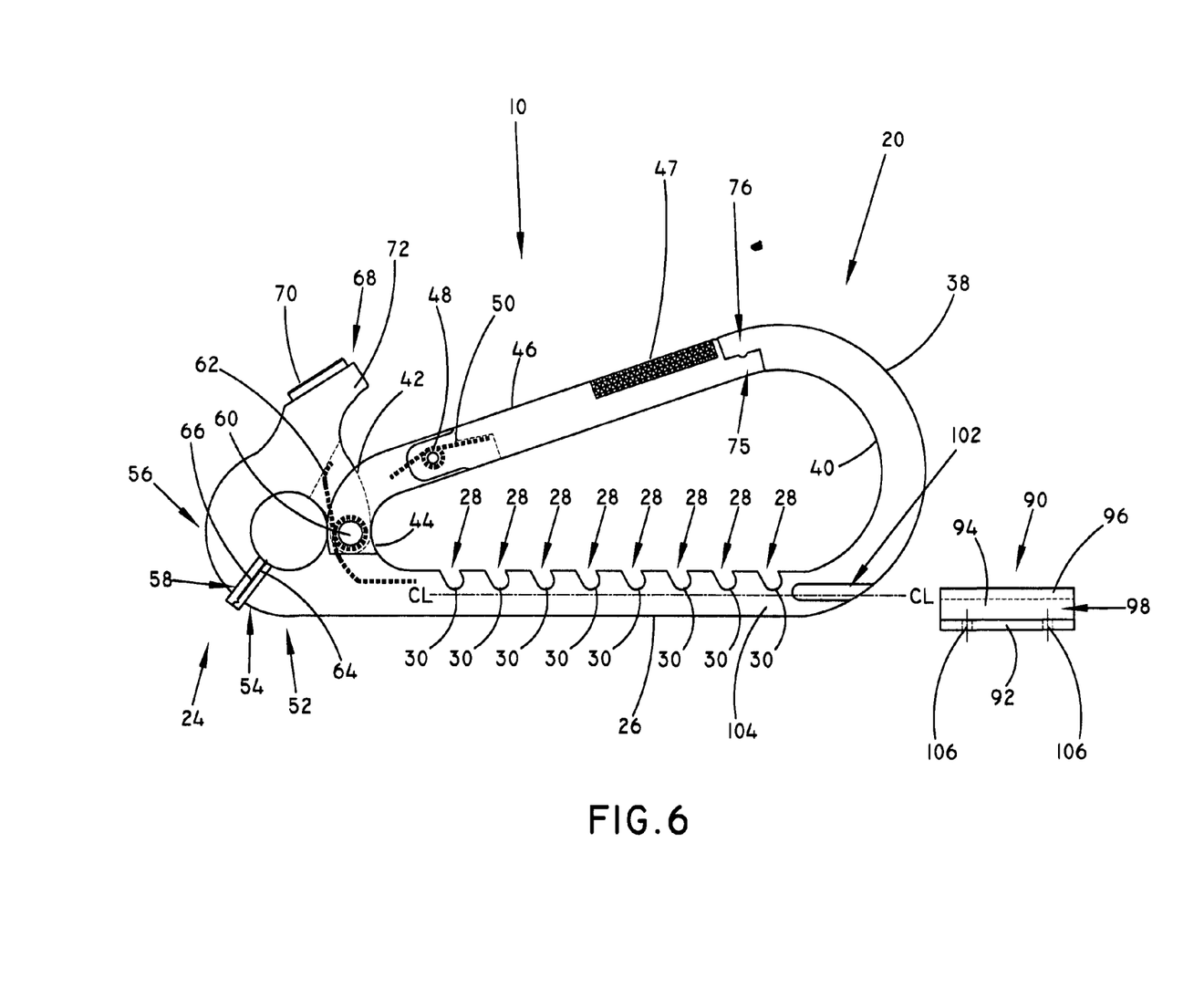
FIG. 6 is an exploded side view of an alternate embodiment of the surgical retainer device of the present invention.
Figure 8:
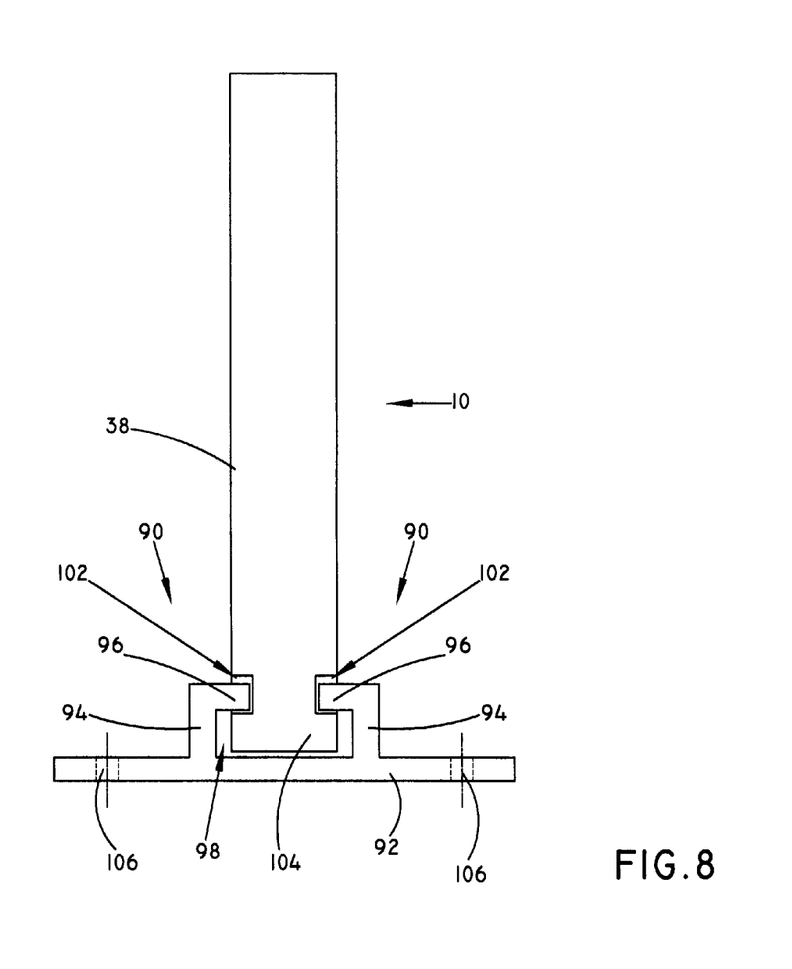
FIG. 8 is an end view of the surgical retainer device of the present invention shown in FIGS. 6 and 7.
Figure 9:
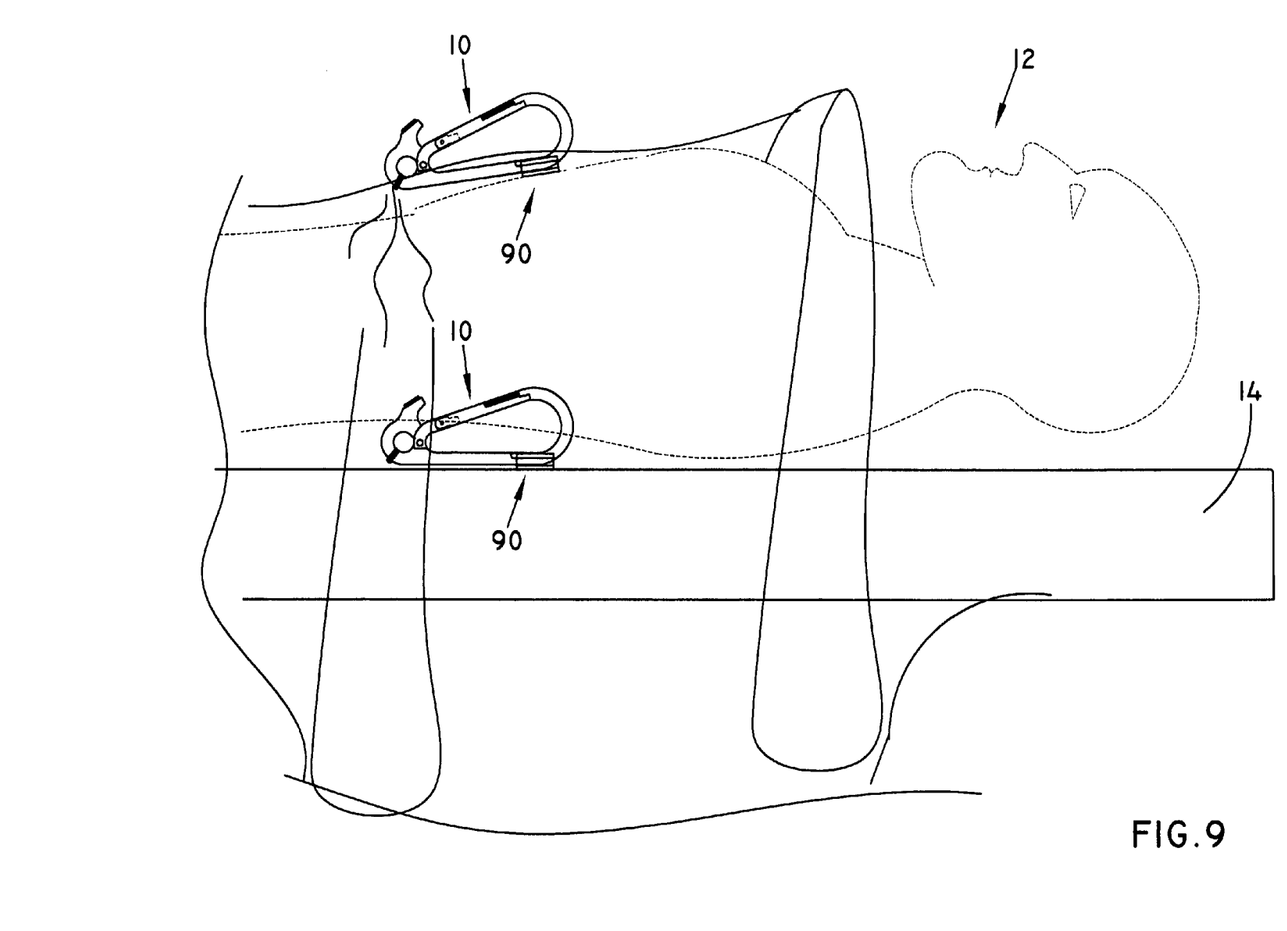
FIG. 9 is a side view of a patient on an operating table protected by a surgical drape with the surgical retainer device of the present invention in use.

FIGS. 6 and 8 depict an alternate embodiment of the suture organizer 10 of the present invention with similar structural components or elements similarly designated. Specifically, the suture organizer 10 comprises a hemostat retainer generally indicated as 20 to retain a plurality of surgical clamps or hemostats each generally indicated as 22 (shown in FIGS. 1 and 2) and a clasp generally indicated as 24 to clamp the suture organizer 10 to the surgical drape 16 (shown in FIGS. 1 and 2).

The hemostat retainer 20 comprises hemostat retainer member 26 having a plurality of grooves each indicated as 28 each terminating in an inner concave terminus 30 to receive a finger hole 32 or a thumb hole 34 of a surgical clamp or hemostat 22 gripping a suture 36 attached to the patient as described more fully hereinafter. Each groove 28 is inclined on a diagonal line relative to the longitudinal center-line CL of the hemostat retainer member 26. An enlarged arcuate substantially U-shaped member 38 having a substantially concave inner surface 40 is formed on one end portion of the hemostat retainer member 26; while, a reduced arcuate substantially C-shaped member 42 having a substantially concave inner surface 44 is formed on the opposite end portion of the hemostat retainer member 26. A retainer closure member 46 including knurled or rough surface 47 formed on the outer or free end portion thereof is pivotally coupled to the reduced arcuate substantially C-shaped member 42 by a pivot pin 48 and biased in a normally closed position by a bias or spring 50 to engage and interlock with the enlarged substantially U-shaped member 38 as described more fully hereinafter.

The clasp 24 comprises a first clasp member generally indicated as 52 formed on the hemostat retainer member 26 adjacent the reduced arcuate substantially C-shaped member 42 having a first grasping element generally indicated as 54 formed thereon and a second clasp member generally indicated as 56 having a second grasping element generally indicated as 58 pivotally coupled to the reduced arcuate substantially C-shaped member 42 by a pivot pin 60 and biased in a normally closed position by a bias or spring 62 such that the first grasping element 54 and the second grasping element 58 grasp or clamp the surgical drape 16 therebetween to attach the suture organizer 10 to the surgical drape 16. The first grasping element 54 and the second grasping element 58 include a knurled or rough surface indicated as 64 and 66 respectively to increase or enhance the grasping or clamping effect therebetween on the surgical drape 16. An actuator or opening member generally indicated as 68 including a knurled or rough surface 70 is formed on an extension 72 formed on the second clasp member 56 to facilitate movement or opening of the second clasp member 52 to separate the first grasping element 54 and the second grasping element 58 relative to each other to create a space 74 therebetween to receive the surgical drape 16 therebetween.

The hemostat retainer 20 may further comprise an interlocking mechanism including a first interlocking element generally indicated as 75 formed on the outer end portion of the enlarged arcuate substantially U-shaped member 38 and a second interlocking element generally indicated as 76 formed on the outer end portion of the retainer closure member 46.

The first interlocking element 75 and the second interlocking element 76 include a first indentation 78 having a recess 80 formed in the mid-portion of the inner surface 82 thereof and a second indentation 84 having a protrusion 86 formed on the mid portion of the inner surface 88 thereof respectively such that the inner surfaces 82 and 88 engage each other and the protrusion 86 is disposed within the recess 80 to align the retainer closure member 46 with the outer end portion of the enlarged substantially U-shaped member 38 when the retainer closure member 46 is in the closed position under the force of the bias or spring 50.

The clasp 24 may further comprise an interlocking mechanism including a first interlocking element or recess 90 formed in the first grasping element 54 and a second interlocking or alignment element or protrusion 92 formed on the second grasping element 58 such that the first grasping element 54 and the second grasping element 58 engage each other and the protrusion 92 is disposed within the recess 90 to align the first grasping element 54 and the second grasping element 58 relative to each other when the second clasp member 56 is in the closed position under the force of the bias or spring 62.

The suture organizer 10 of the alternate embodiment shown in FIGS. 6 and 8 further includes structure to retain or secure the suture organizer 10 in place during a medical procedure. Specifically, the retainer device comprises a retainer member generally indicated as 90 including a base 92 having a pair of substantially parallel retainer legs each indicated as 94 extending upwardly therefrom each terminating in an upper guide or retainer element 96 extending inwardly from the corresponding leg retainer 94 such that the pair of substantially parallel retainer legs 94 and the upper guide or retainer elements 96 to cooperatively form a retainer channel 98 therebetween. The space between the inner ends of the upper guide or retainer elements 96 cooperatively form a retainer slot 100. A longitudinal retainer groove 102 is formed on each side of the hemostat retainer 20 adjacent the enlarged arcuate substantially U-shaped member 30 to slidingly receive the corresponding upper guide or retainer element 96 therein such that the lower end portion 104 of the hemostat retainer member 26 is retained in the retainer channel 98. A plurality of securing or fastening holes or apertures each indicated as 106 are formed in the base 92 to receive a corresponding fastener (not shown) therethrough to secure the retainer member 90 and the suture organizer 10 to the operating table 14 or other surface.

Figure 7:
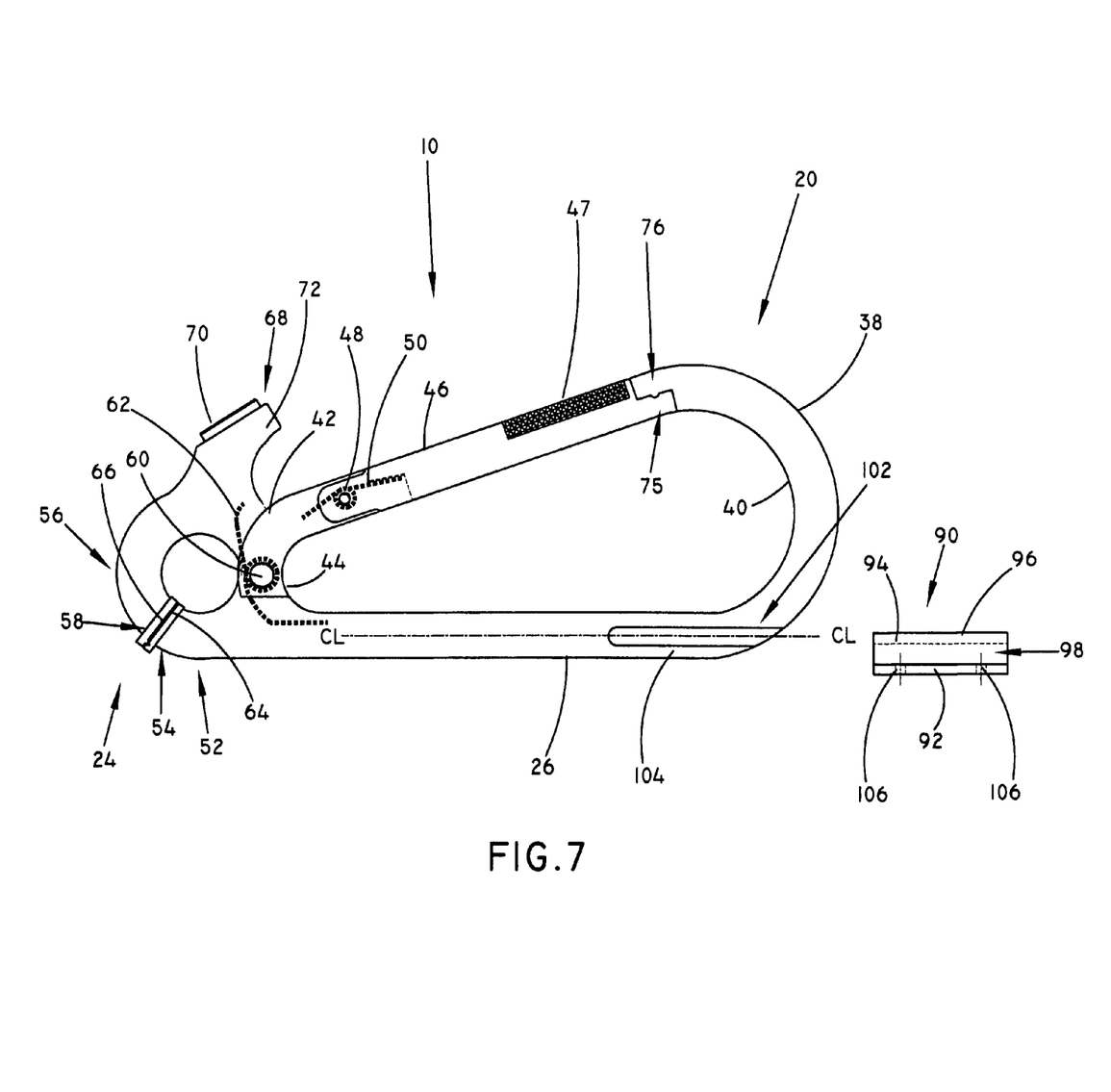
FIG. 7 is an exploded side view of another alternate embodiment of the surgical retainer device of the present invention.

FIGS. 7 and 8 depict another alternate embodiment of the suture organizer 10 of the present invention with similar structural components or elements similarly designated. Specifically, the suture organizer 10 comprises a hemostat retainer generally indicated as 20 to retain a plurality of surgical clamps or hemostats each generally indicated as 22 (shown in FIGS. 1 and 2) and a clasp generally indicated as 24 to clamp the suture organizer 10 to the surgical drape 16 (shown in FIGS. 1 and 2).

The hemostat retainer 20 comprises hemostat retainer member 26 to receive a finger hole 32 or a thumb hole 34 of a surgical clamp or hemostat 22 gripping a suture 36 attached to the patient as described more fully hereinafter. An enlarged arcuate substantially U-shaped member 38 having a substantially concave inner surface 40 is formed on one end portion of the hemostat retainer member 26; while, a reduced arcuate substantially C-shaped member 42 having a substantially concave inner surface 44 is formed on the opposite end portion of the hemostat retainer member 26. A retainer closure member 46 including knurled or rough surface 47 formed on the outer or free end portion thereof is pivotally coupled to the reduced arcuate substantially C-shaped member 42 by a pivot pin 48 and biased in a normally closed position by a bias or spring 50 to engage and interlock with the enlarged substantially U-shaped member 38 as described more fully hereinafter.

The clasp 24 comprises a first clasp member generally indicated as 52 formed on the hemostat retainer member 26 adjacent the reduced arcuate substantially C-shaped member 42 having a first grasping element generally indicated as 54 formed thereon and a second clasp member generally indicated as 56 having a second grasping element generally indicated as 58 pivotally coupled to the reduced arcuate substantially C-shaped member 42 by a pivot pin 60 and biased in a normally closed position by a bias or spring 62 such that the first grasping element 54 and the second grasping element 58 grasp or clamp the surgical drape 16 therebetween to attach the suture organizer 10 to the surgical drape 16. The first grasping element 54 and the second grasping element 58 include a knurled or rough surface indicated as 64 and 66 respectively to increase or enhance the grasping or clamping effect therebetween on the surgical drape 16. An actuator or opening member generally indicated as 68 including a knurled or rough surface 70 is formed on an extension 72 formed on the second clasp member 56 to facilitate movement or opening of the second clasp member 52 to separate the first grasping element 54 and the second grasping element 58 relative to each other to create a space 74 therebetween to receive the surgical drape 16 therebetween.

The hemostat retainer 20 may further comprise an interlocking mechanism including a first interlocking element generally indicated as 75 formed on the outer end portion of the enlarged arcuate substantially U-shaped member 38 and a second interlocking element generally indicated as 76 formed on the outer end portion of the retainer closure member 46.

The first interlocking element 75 and the second interlocking element 76 include a first indentation 78 having a recess 80 formed in the mid-portion of the inner surface 82 thereof and a second indentation 84 having a protrusion 86 formed on the mid portion of the inner surface 88 thereof respectively such that the inner surfaces 82 and 88 engage each other and the protrusion 86 is disposed within the recess 80 to align the retainer closure member 46 with the outer end portion of the enlarged substantially U-shaped member 38 when the retainer closure member 46 is in the closed position under the force of the bias or spring 50.

The clasp 24 may further comprise an interlocking mechanism including a first interlocking element or recess 90 formed in the first grasping element 54 and a second interlocking or alignment element or protrusion 92 formed on the second grasping element 58 such that the first grasping element 54 and the second grasping element 58 engage each other and the protrusion 92 is disposed within the recess 90 to align the first grasping element 54 and the second grasping element 58 relative to each other when the second clasp member 56 is in the closed position under the force of the bias or spring 62.

The suture organizer 10 of the alternate embodiment shown in FIGS. 7 and 8 further includes structure to retain or secure the suture organizer 10 in place during a medical procedure. Specifically, the retainer device comprises a retainer member generally indicated as 90 including a base 92 having a pair of substantially parallel retainer legs each indicated as 94 extending upwardly therefrom each terminating in an upper guide or retainer element 96 extending inwardly from the corresponding retainer leg 94 such that the pair of substantially parallel retainer legs 94 and the upper guide or retainer element 96 to cooperatively form a retainer channel 98 therebetween. The space between the inner ends of the upper guide or retainer elements 96 cooperatively form a retainer slot 100. A longitudinal retainer groove 102 is formed on each side of the hemostat retainer 20 adjacent the enlarged arcuate substantially U-shaped member 30 to slidingly receive the corresponding upper guide or retainer element 96 therein such that the lower end portion 104 of the hemostat retainer member 26 is retained in the retainer channel 98. A plurality of securing or fastening holes or apertures each indicated as 106 are formed in the base 92 to receive a corresponding fastener (not shown) therethrough to secure the retainer member 90 and the suture organizer 10 to the operating table 14 or other surface.

Once the surgeon has attached the sutures 36 to the patient 12, each suture 36 with the corresponding surgical clamp or hemostat 22 secured thereto is extended away from the surgical field 18. With the retainer closure member 46 held open against the force of the bias or spring 50 (FIG. 4), the surgical clamps or hemostats 22 are positioned on the hemostat retainer member 26 with the finger hole 32 or thumb hole 34 placed into a corresponding groove 30. Once so positioned, the retainer closure member 46 is released allowing the force of the bias or spring 50 to close the retainer closure member 46 such that the first interlocking element 75 and the second interlocking element 76 operatively engage each other. The free end of each suture 36 having the surgical clamp or hemostat 24 attached thereto is allowed to rest more or less freely, the weight provided by the surgical clamp or hemostat 24 in cooperation with the suture organizer 10 being sufficient to tension the sutures 36 and prevent adjacent sutures 36 from becoming entangled (FIGS. 1 and 2).

The suture organizer 10 is attached or secured to the surgical drape 16 by depressing the actuator or opening member 68 to separate the first grasping element 54 from the second clasping element 58 against the force of the bias or spring 62 (FIG. 5). When the clasp 24 is open, a portion of the surgical drape 16 is placed into the opening 74 between the first grasping element 54 and the second clasping element 58 (FIG. 5). The actuator or opening member 68 is then released allowing the bias or spring 62 to close the second clasp member 56 such that the first grasping element 54 and the second clasping element 58 engage each other and the second interlocking element or protrusion 92 is disposed with the first interlocking element or recess 90 grasping the surgical drape 16 therebetween.

To aid the surgeon in identifying individual sutures 36, identifying indicia such as numerals or numbers may be placed on the surface of the hemostat retainer 26 adjacent each of the grooves 28 (FIG. 5). In addition, the indicia can be color coded such as coloring dots or letters or numbers may be color-coded, or combinations of each.

The surgical clamps or hemostats 22 are removed in order from the hemostat retainer 20 of the suture organizer 10 by opening the retainer closure member 46 and reversing the process.

It will thus be seen that the objects set forth above, among those made apparent from the preceding description are efficiently attained and since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A suture organizer to maintain a plurality of hemostats in spaced relationship relative to each other attached by corresponding sutures to a patient during a surgical procedure or operation, said suture organizer comprising: a hemostat retainer including a hemostat retainer member including a longitudinal centerline and a plurality of grooves formed in the surface thereof, each said groove terminating in a seat to receive the finger hole or thumb hole of a corresponding hemostat connected to a corresponding suture and a clasp movable between an open position and a closed position normally biased in said closed position including a pair of clasp members to cooperatively clamp a surgical drape or the like therebetween to hold the suture organizer in position during the surgical procedure or operation when in said closed position wherein each said groove includes a centerline diagonally inclined relative to said longitudinal centerline of said hemostat retainer member to retain each hemostat within said corresponding groove in spaced relationship relative to the adjacent hemostat.

2. The suture organizer of claim 1, further comprising a retainer device to retain said suture organizer in place during a surgical procedure or operation.

3. The suture organizer of claim 2, wherein said retainer device comprises a base having at least one retainer leg extending upwardly therefrom terminating in a retainer element extending inwardly from said leg and said hemostat retainer includes a longitudinal retainer groove formed thereon to slidingly receive said corresponding retainer element to secure said suture organizer to an operating table or other surface.

4. The suture organizer of claim 3, further including a plurality of securing apertures formed in said base to receive a corresponding fastener therethrough to secure said retainer member and said suture organizer to an operating table or other surface.

5. The suture organizer of claim 2, wherein said retainer device comprises a retainer member including a base having a pair of substantially parallel retainer legs extending upwardly therefrom, each said retainer leg terminating in a retainer element extending inwardly therefrom such that said pair of substantially parallel retainer legs and said retainer element cooperatively form a retainer channel therebetween and a slot is cooperatively formed between the inner ends of said retainer elements and said hemostat includes a longitudinal retainer groove formed on each side thereof to slidingly receive a corresponding retainer element therein to secure said suture organizer during a surgical procedure or operation.

6. The suture organizer of claim 1, wherein said hemostat retainer further includes an enlarged arcuate member formed on one end portion of said hemostat retainer member and a reduced arcuate member is formed on the opposite end portion of said hemostat retainer member.

7. The suture organizer of claim 6, further including a retainer closure member is pivotally coupled to said reduced arcuate member by a pivot pin and biased in a normally closed position to engage said enlarged arcuate member.

8. The suture organizer of claim 7, wherein said hemostat retainer further comprises an interlocking mechanism including a first interlocking element formed on the outer end portion of said enlarged arcuate member and a second interlocking element formed on the outer end portion of said retainer closure member.

9. The suture organizer of claim 8, wherein said first interlocking element includes a first indentation having an inner surface and said second interlocking element includes a second indentation having an inner surface, said inner surface of said first indentation and said inner surface of said second indentation disposed to engage each other in parallel relationship when said retainer closure member is in said normally closed position.

10. The surgical organizer of claim 9, wherein said inner surface of said first indentation includes a recess formed in the mid-portion thereof and said inner surface of said second indentation includes a protrusion formed on the mid-portion thereof such that when said inner surfaces engage each other said protrusion is disposed within said recess to align said closure member with said outer end portion of said enlarged arcuate member.

11. The suture organizer of claim 7, wherein said retainer closure member includes a knurled or rough surface formed on the distal end portion thereof.

12. The suture organizer of claim 1, further including a clasp comprising a first clasp member formed on said hemostat retainer member adjacent said reduced member having a first grasping element formed thereon and a second clasp member having a second grasping element pivotally coupled to said reduced member and biased in a normally closed position such that said first grasping element and said second grasping element grasp or clamp the surgical drape therebetween to attach said suture organizer to the surgical drape.

13. The suture organizer of claim 12, wherein said first grasping element and said second grasping element each includes a rough surface to increase the grasping or clamping effect therebetween on the surgical drape.

14. The suture organizer of claim 12, wherein an opening member includes a rough surface formed on an extension on said second clasp member to facilitate movement or opening of the second clasp member to separate the first grasping element and said second grasping element relative to each other to create a space therebetween to receive the surgical drape therebetween.

15. The suture organizer of claim 12, wherein said clap further comprises an interlocking mechanism including a first interlocking element formed in said first grasping element and a second interlocking element formed in said second grasping element, said first interlocking element and said second interlocking element disposed to engage each other to align said first grasping element and said second grasping element relative to each other when said second clasp member is in said closed position.

16. The suture organizer of claim 15, wherein said first interlocking element comprises a protrusion and said second interlocking element comprise a recess to receive said protrusion when said second clasp member is in said closed position.

17. The suture organizer of claim 1, wherein said seat of each said groove comprises an inner concave terminus to receive a finger hole or a thumb hole of the corresponding hemostat.

18. A suture organizer to maintain a plurality of sutures attached to a patient during a surgical procedure or operation in position relative to each other during the surgical procedure or operation, said suture organizer comprising: a hemostat retainer member having a longitudinal centerline and a plurality of grooves formed in the surface thereof to receive and retain the finger hole or thumb hole of a corresponding hemostat connected to a corresponding suture, wherein each said groove includes a centerline diagonally inclined relative to said longitudinal centerline of said hemostat retainer member to retain each hemostat within said corresponding groove in space relationship relative to the adjacent hemostat, said hemostat retainer member including a proximal end portion and a distal end portion disposed in spaced relationship relative to each other, a retainer closure member including a proximal end portion and a distal end portion pivotally coupled to said proximal end portion of said hemostat retainer member and biased in a normally closed position to engage said distal end portion of said hemostat retainer member; and a retainer device to retain said suture organizer in place during a surgical procedure or operation, and said retainer device comprising a retainer member including a base having a pair of substantially parallel retainer legs extending upwardly therefrom, each said retainer leg terminating in a retainer element extending inwardly therefrom such that said pair of substantially parallel retainer legs and said retainer element cooperatively form a retainer channel therebetween and a slot is cooperatively formed between the inner ends of said retainer elements and said hemostat includes a longitudinal retainer groove formed on each side thereof to slidingly receive a corresponding retainer element therein to secure said suture organizer during a surgical procedure or operation.

* * * * *